United States Patent [19]

Blank

[11] Patent Number: 5,242,905

[45] Date of Patent: Sep. 7, 1993

[54] PHARMACEUTICAL COMPOSITIONS FOR THE TREATMENT OF PSORIASIS

[75] Inventor: Izhak Blank, Kiriat Onu, Israel

[73] Assignee: Dexter Chemical Corporation, Bronx, N.Y.

[21] Appl. No.: 732,342

[22] Filed: Jul. 17, 1991

Related U.S. Application Data

[63] Continuation of Ser. No. 239,675, Sep. 2, 1988, abandoned.

[30] Foreign Application Priority Data

Sep. 4, 1987 [IL] Israel ........................................ 83775

[51] Int. Cl.$^5$ ............................................... A61K 37/02
[52] U.S. Cl. ....................................................... 514/19
[58] Field of Search ........................... 514/19; 560/169

[56] References Cited

U.S. PATENT DOCUMENTS

| 3,458,304 | 7/1969 | Hageman et al. | 560/169 |
| 3,950,392 | 4/1976 | D'Alelio | 560/169 |

FOREIGN PATENT DOCUMENTS

| 778342 | 6/1965 | Canada . |
| 0188749A2 | 12/1985 | European Pat. Off. . |
| 2530372A1 | 7/1975 | Fed. Rep. of Germany . |
| 2621214C3 | 5/1976 | Fed. Rep. of Germany . |
| 2840498 | 9/1978 | Fed. Rep. of Germany . |
| 2901452 | 1/1979 | Fed. Rep. of Germany . |
| 3232883A1 | 9/1982 | Fed. Rep. of Germany . |
| 1586682 | 7/1968 | France . |

OTHER PUBLICATIONS

A. Lahti et al., Contact Dermatitis, 12, 139–140 (1985).
A. Lahti et al., "Pharmaceutical Studies on Nonimmunologic Contact Urticaria In Guinea Pigs", Arch. Dermatol. Res., 299, 44–49 (1986).
W. Raab, H&G Nr. 10 (1984).
Lahty et al., Contact Dermatitis 3, 139–140 (1985).
Schafer G., Fumarsauretherapie der Psoriasis, Arztliche Praxis 30, 61, 1757–58 (1978).
Selecta 15, 1260–61 (1984).
Thaler et al., J. Invest. Dermatol. 75, 156–158 (1980).
Steinert et al., Biochemistry of Normal and Abnormal Differentiation, eds. I. A. Bereinstein and M. Seiji, Tokyo University Press, pp. 391–406 (1980).
J. Marach, Advanced Organic Chemistry, 3d ed., p. 339, J. Wiley and Sons, New York (1985).
Lochmueller, C. H. et al., Direct gas chromatographic resolution of enantiomers on optically active mesophases. IV. Effect of structure on selectivity and liquid crystalline behavior, J. Chromat. 178, 411–417 (1979).
Meek, J. L., Derivatizing reagents for high-performance liquid chromatography detection of peptides at the picomole level, J. Chromat. 266, 401–408 (1983).
Augustin, M., N-Maleyl amino acids and peptides, Z. Chem. 25, 18–19 (1985).
Portoghese, P. S. et al., Synthesis and opioid antagonist potencies of Naltrexamine Bivalent Ligands with Conformationally Restricted Spacers, J. Med. Chem. 29, 1650–1653 (1986).
Schellenberger, V. et al., A spectrophotometric assay for the characterization of the S' subsite specificity of α-chymotrypsin, Bioch. et Bioph. Acta 869, 54–60 (1986).
Nieboer C. et al., Systemic therapy with fumaric acid derivatives: New possibility in the treatment of psoriasis, J. Am. Acad. Derm. 20, 601–607 (1989).
Chemical Abstract No. 83-114855b.

*Primary Examiner*—Lester L. Lee
*Attorney, Agent, or Firm*—Curtis Morris & Safford

[57] ABSTRACT

The invention comprises compositions and methods for the treatment of psoriasis. The compositions comprise compounds of the formula:

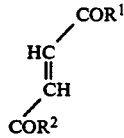

1 Claim, No Drawings

PHARMACEUTICAL COMPOSITIONS FOR THE TREATMENT OF PSORIASIS

This application is a continuation of application Ser. No. 239,675, filed Sept. 2, 1988, and now abandoned.

BACKGROUND OF THE INVENTION

Psoriasis is one or the most widespread chronic diseases. It affects about two percent of the adult white population, the most severe symptoms being shown by patients in the age groups between twenty and fifty years old.

Psoriasis is characterized by a greatly accelerated rate of epidermal turnover. Instead of the normal period of 28 days from the time of cell division in the basal layers until the cell is shed from the stratum corneum, in psoriasis this takes only about four days.

The causes and mechanism of development of psoriasis are unknown, and for this reason a completely effective treatment for this ailment does not yet exist. A great number of approaches have been tried, from the very old, based on natural tars, to the more modern using steroids, sporalene, etc. Tars are messy to apply and have only a limited effect. Their combination with sulfur and salicylic acid are not much better. This therapy is frequently supplemented by the use of ultraviolet (UV) radiation, either natural (sunshine) or artificial (lamps). Other compounds used are: steroids, azaribine, methotrexate, psoralen, and retinoic acid derivatives. All of these have a rather high toxicity and their long term use may result in noxious side effects.

A possible approach to the therapy of the disease is to try to influence cellular metabolism, which obviously is much more active in the psoriatic cells than in the normal ones.

A few years ago, a new treatment was proposed. This is based on the use of fumaric acid in the form of its simple mono- or diesters or its metal salts, based on the theory that in the psoriatic portions of the skin there exists an unbalance in the dicarboxylic-acids cycle conducive to lower levels of fumarate. This theory seems to be confirmed by the fact that some amino acids, such as glycine, are present in lower quantities in the psoriatic skin, compared to their content in normal skin. Since these amino acids are also derived from the dicarboxylic-acids cycle, their presence in lower quantities is an added corroboration to the above theory.

A number of patent applications deal with the use of fumarate esters and salts for the treatment of psoriasis. GP 2530372 (13.1.77) describes the use of fumaric acid, fumarate esters, such as monoethyl and monomethyl fumarate, dimethyl fumarate; some salts of the monoesters such as manganese, calcium, zinc, iron, etc. All of these can be mixed with other ingredients such as tartaric acid, citric acid, sugar, and inert fillers. Some of these formulations are for internal use and some for external (topical) application. Related applications, GP 2840498 (10.4.80) and GP 2901452 (17.7.80), describe the addition of glycine, 1-methionine, and 1-cysteine to the above mixtures of fumarate esters and salts. A recent European patent, 0188749 A2 (30.7.86) claims the use of fumarate esters of alcohols having one to eight carbon atoms, esters of higher alcohols (C6–C24), metal salts of the monoesters, and esters of diols, glycerol, and other hydroxyl-containing compounds. Another patent, GP DE 3232883 A1 mentions the preparation of salts of fumaric acid with various caffein-8-ethers. The salts are crystalline and can be used for the preparation of tablets, capsules, etc., in combination with metal salts of fumaric esters, as mentioned before, and also with the optional addition of amino acids such as cysteine and methionine, and of vitamin C.

There exist serious problems as to the use of the above in the therapy of psoriasis. Short-chain fumarate esters are in general irritating materials which frequently produce an unpleasant acidosis effect upon ingestion. Metal salts of the half esters are quickly converted in the stomach into the free acid and the respective metal hydrochloride. The same happens with the caffein-ether salt. The esters are liquid at room temperature and in order to convert them to tablets they have to be adsorbed on, or mixed with, a rather large quantity of inert carrier. Furthermore, they have a strong characteristic odor and their toxicology has not been studied extensively. According to a study made with mice, monoethyl fumarate and dimethyl fumarate given per os had an $LD_{50}$ above 100 mg/kg. Monoethyl fumarate, given intraperitoneally, was more toxic (W. Raab, H&G Nr. 10 (1984)). These fumarate esters are highly irritating to the skin and can produce contact urticaria (A. Lahti et al., Contact Dermatitis, 12, 139–140 (1985)).

To summarize: mono and diesters of fumaric acid have been shown to be effective in the treatment of psoriasis, as the experience with several thousand patients indicates (see, for instance: Schafer G. Fumarsauretherapie der Psoriasis, Arztliche Praxis 30, 61 p. 1757–58 (1978); also, Selecta 15, p. 1260–61 (1984)). The esters are irritating to the digestive system and to the skin and their toxicology has not been clearly established; they are also difficult to formulate as tablets.

Recent studies have shown that in psoriatic skin the content of glycine and serine is about twenty-five percent lower than in normal skin (Thaler et al., J. Invest. Dermatol. 75, 156–158 (1980); also, Steinert et al., Biochemistry of Normal and Abnormal Epidermal Differentiation, eds. I. A. Bereinstein and M. Seiji, Tokyo University Press, p. 391–406 (1980)). This deficiency may be related to the fumarate imbalance or to other unknown causes. The addition of glycine as such, to such formulations, cannot contribute much to the therapeutic effect since this water-soluble material will be quickly incorporated into the general metabolic processes, so, at best, its value will be like an added food.

BRIEF DESCRIPTION OF THE INVENTION

We have found that linking amino acids such as glycine, serine, etc., to fumaric acid via a chemical link such as via amide groups, results in conjugates which have a high efficacy in the treatment of psoriasis. The conjugate compounds are mostly stable crystalline solids. They are easy to formulate as tablets, ointments, or similar galenic forms. The amide bond is known to be more stable to hydrolysis than an ester group (see, for instance, J. March, Advanced Organic Chemistry 3rd ed. p. 339, J. Wiley & Sons, New York (1985)), and therefore the fumar-amido amino acids are converted at a much slower rate into the fumarate and the free amino acid. They are easily absorbed through the digestive system, since it is known that amides have good solubilization properties both with hydrophilic and lipophilic compounds.

In its broadest aspects, therefore, the invention relates to compositions and methods for delivering a residue of fumaric acid and one or more amino acids to humans. It has been found that the compositions of the invention alleviate the symptoms of psoriasis. It has also been found that the compositions of the invention when administered per os have the effect of stimulating digestion and appetite, and when administered per os or topically reduce the tanning effects of the sun.

DETAILED DESCRIPTION OF THE INVENTION

The compounds of the invention include compounds of the formula

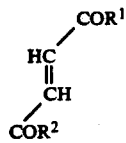

wherein $R^1$ and $R^2$, which are the same or different, each designates
- (a) (i) a residue of an amino acid, provided that both $R^1$ and $R^2$ are not residues of glycine,
  (ii) an ester of an amino acid,
  (iii) a salt of an amino acid, or
  (iv) a peptide of two or more amino acids, or
- (b) a residue of an amino compound selected from the group consisting of lower alkylamines wherein the alkyl group contains up to 10 carbon atoms, alkarylamines, or arylamines, or
- (c) an OH group, provided that only one of said $R^1$ and $R^2$ may be OH, or a pharmaceutically acceptable salt thereof.

In accordance with the invention, there are provided fumarate amido-amino acid compounds wherein the amino acids are selected from one or more of: glycine, serine, proline, valine, histidine, methionine, threonine, leucine, isoleucine, cysteine, cystine, methionine, phenylalanine, tyrosine, proline, hydroxyproline, tryptophan, aspartic acid, glutamic acid, histidine, lysine, and arginine, as well as their derivatives, such as esters, salts, etc. Thus, for instance, it is possible to use in the formulations the fumaramide of ethyl glycinate or of sodium glycinate. In other words, it is possible to make use of the carboxylic acid group of the amino acid to further change the solubility and other characteristics of the compound. Furthermore, since fumaric acid has two carboxyl groups, it is possible to prepare and make use of mixed amides, such as the glycine, serine fumaramide. Further still, it is possible to prepare and make use of fumaramides which are substituted by peptides comprising two or more amino acid residues such as di-(serine-glycine)-fumaramide and di-(glycine-serine)-fumaramide.

The amino acid esters of the compounds are desirably lower alkyl esters containing from 1 to 4 carbon atoms in the alkyl group. Where $R^1$ or $R^2$ is an alkylamine, the alkyl group may contain broadly up to 24 carbon atoms, or, more narrowly, up to 10 carbon atoms. By using in the synthesis long-chain amines, it is possible to obtain fumaramides of particular interest for topical use. Suitable compounds are the amides of n-octylamine, 2-ethyl-hexyl amine, dodecylamine, octadecylamine, etc., in the form of simple and mixed diamides, or in combination with the amino acids and substituted amino acids as mentioned above. The introduction of long-chain amines into the molecule makes the resulting materials more lipophilic, and thus enhances the rate of transdermal penetration.

The compositions of the invention may contain the active compounds described above, as well as compounds wherein $R^1$ and $R^2$ are glycine and alkylamine containing up to 24 carbon atoms, together with a pharmaceutically acceptable carrier as are known in the art. The carriers may include vehicles for immediate or sustained release and may be in a variety of dosage forms as are also known in the art.

The methods of the invention include, broadly, a method for delivering residues of fumaric acid and/or amino acids to a patient by administering the compositions of the invention, either per os or topically, as circumstances dictate. The compositions of the invention may be used to alleviate the symptoms of psoriasis. They may also be used to stimulate the appetite, and to reduce the tanning effects of the sun.

The materials of this invention are nonirritating to the skin, and preliminary toxicological studies with the diglycyl fumaramide show the $LD_{50}$ to be above 10 gr/kg (per os in rats). The diethyl ester of diglycyl fumaramide showed an $LD50$ above 5 gr/kg. The amide conjugates are mild and nonirritating. Glycine is used in some formulations of aspirin tablets with the object of reducing gastric irritation. Any amount of glycine produced in the stomach by hydrolysis of the amide, will actually act in a beneficial way, in this respect.

The invention is illustrated by the following examples which are not limiting.

EXAMPLES

All quantities are given in parts by weight.

Example 1:=Diglycyl fumaramide (GFA)

Glycine 165 parts, were added to 180 parts of sodium hydroxide dissolved in 720 parts of water. The solution was cooled and to it were added, under stirring, 168 parts of fumaryl chloride. After completion of the reaction, the product was acidified and purified by washing with water, filtered and dried to obtain the amide acid in the form of a light tan unctuous powder. M.P.=260–270° C. (dec). N(calc) 12.17%; found: 12.30%. The material was further characterized by NMR.

Example 2:=Lauryl fumaramide (LFA)

Fumaryl chloride 53.2 parts, lauryl (dodecyl) amine 43.3 parts, and 37 parts of sodium hydroxide, in the form of an aqueous solution, were used. The procedure was similar to the one described in Example 1. The product is a soft wax.N(calc.)=6.20%, found: 6.18%.

Example 3:=Serine fumaramide (SFA)

This was similarly made by using serine 8 parts, fumaryl chloride 6.2, and sodium hydroxide 6.65 as a solution in water. The material is waxy, light yellow in color. N(calc.)=9.6%; found: 9.4%.

Example 4:=Glycyl-lauryl fumaramide (GLFA)

Glycine 4.5 parts, dodecylamine 11.1 parts, fumaryl chloride 19.3 parts, and sodium hydroxide 8 parts, as an aqueous solution, were reacted as in Example 1. Obtained an off-white waxy material. N(calc.)8.2%; found: 7.9%.

Example 5:=Ethyl ester of diglycyl fumaramide (EGFA)

Glycine ether ester hydrochloride 13.9 parts, fumaryl chloride 7.65 parts, and 8.8 parts of sodium hydroxide in water were reacted as above. After purification the material obtained is an off-white powder. N(calc.)9.7; found: 10.1.

GALENIC FORMS

Example 6:=Capsules

Pure GFA prepared as per Example 1 was put in gelatin capsules (100 mg. each) and these were given to patients suffering from psoriasis, at an initial rate of 3 capsules a day and going up to 8 capsules a day, if necessary, the exact amount depending on the individual patient. After several weeks of this therapy the lesions started to disappear. No side effects were noticed.

Example 7:=Tablets

The same material was granulated with 1% polyvinylpyrrolidinone and 0.2% magnesium stearate and then compressed into tablets. These were hard and nonfriable. Example 8:=Gel GFA 40 parts, propylene glycol 30, isopropyl myristate 4, cetyl alcohol 6, and ethanol 22, were mixed well. The resulting gel had a viscosity of 30,000 cps (Brookfield). It was packed in tubes and used for the topical treatment of psoriasis patients. After only two weeks of treatment descamation was noticed as well as a beginning of healing.

The same material was used with good results for the treatment of a patient with a localized hyperkeratosis. After about one week of twice a day application, the skin was smooth and free of scales.

Example 9:=Gel

LFA prepared as per Example 2, 38.4 parts were mixed with 12.1 ceryl alcohol, 11.4 isopropyl myristate, 11.6 propylene glycol, 20.1 ethanol, and 1.4 silica. The resulting gel was packed in tubes and used for the topical treatment of psoriatic wounds.

Example 10:=Gel

A gel was prepared as described in Example 9 but using the material of Example 4 (GLFA).

Example 11:=Shampoo

The material of Example 4 (GLFA) has surfactant properties and is a medium foamer. When diluted with water to a 10% concentration it was used as a scalp wash for alleviating psoriatic wounds in that area of the body. At a dilution of 5% it was used as a bath shampoo.

I claim:

1. A pharmaceutical composition which comprises a pharmaceutically effective amount of a compound diglycylfumaramide diethyl ester, of formula

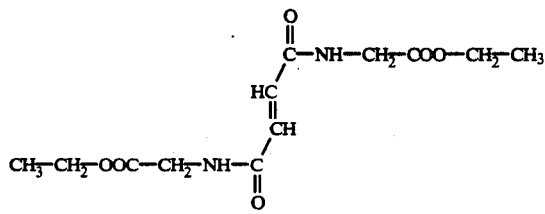

and a pharmaceutically acceptable carrier.

* * * * *